United States Patent [19]

Lloyd et al.

[11] Patent Number: 5,739,081
[45] Date of Patent: Apr. 14, 1998

[54] WATER DISPERSIBLE GRANULES OF LIQUID PESTICIDES

[75] Inventors: John M. Lloyd; Kevin R. Baker, both of Richmond, New Zealand

[73] Assignee: ICI Australia Operations Proprietary Ltd., Melbourne, Australia

[21] Appl. No.: 6,302

[22] Filed: Jan. 22, 1993

[30] Foreign Application Priority Data

Jan. 24, 1992 [NZ] New Zealand .............................. 241387

[51] Int. Cl.$^6$ ...................................................... A01N 25/12
[52] U.S. Cl. ........................ 504/116; 424/405; 71/64.03; 71/DIG. 1
[58] Field of Search ..................................... 504/116, 258; 71/DIG. 1, 64.03; 424/405

[56] References Cited

FOREIGN PATENT DOCUMENTS

| A22130 | 6/1984 | Australia. |
| B59700 | 2/1991 | Australia. |
| 85376 | 8/1983 | European Pat. Off.. |
| 112438 | 7/1984 | European Pat. Off.. |
| 447056 | 1/1991 | European Pat. Off.. |
| 2111620 | 10/1988 | Japan. |

*Primary Examiner*—S. Mark Clardy
*Attorney, Agent, or Firm*—Cushman Darby & Cushman IP Group Pillsbury Madison & Sutro LLP

[57] ABSTRACT

Water dispersible granules suitable for agricultural application are prepared by first preparing absorbent water dispersible granules and then loading biologically active substances into the preformed absorbent granules.

16 Claims, No Drawings

WATER DISPERSIBLE GRANULES OF LIQUID PESTICIDES

TECHNICAL FIELD OF THE INVENTION

This invention relates to water dispersible granules for agricultural use. More particularly, the invention relates to water dispersible granules that carry biologically active substances, in liquid form, including pesticides and/or adjuvants which enable the active substances to be delivered to target species.

BACKGROUND OF THE INVENTION

Biologically active substances for the control of weeds, insects, fungi and other pests are extensively used and are generically referred to as pesticides. They may also include beneficial agents such as plant growth regulators. When the active substances are in a liquid state at ambient temperatures they have been formulated in a number of ways that, to varying extents, are adapted for ease of transport, handling and application. It is generally desirable with these various formulations that the active substance be delivered in the form of an aqueous spray. Examples of types of formulations that may be applied in this manner are emulsifiable concentrates (EC), wettable powders (WP), suspension concentrates (SC) and water dispersible granules (WG). EC, WP and SC formulations have disadvantages either during manufacture, transport, storage or use. Limitations of EC formulations include the dangers in packaging, storing and handling highly flammable solvents. WP formulations can present handling problems with the nuisance and potential health hazard of dust to the user. SC formulations can have storage problems and are difficult to clean up after spillage.

WG formulations offer significant advantages in packaging, ease of handling and safety. Typically these consist of small granules of 0.1–3 mm in diameter and preferably of uniform size and which are free flowing, low dusting and readily disperse in water to form an homogenous suspension of very small particles which may pass through conventional spray nozzles. Ideally WG formulations when dispersed in water under gentle agitation for five minutes have residues of less than 0.01% on a 150 µm sieve screen and less than 0.5% on a 53 µm screen. The granules can usually be measured accurately by volume which is convenient for the end user.

Generally, WG comprise a biologically active substance, a filler (also referred to as diluent), surface active agents (which term may include dispersants and wetting agents) and auxiliary agents such as binders, stabilisers and buffering agents. The amounts of individual ingredients may vary widely, with the biologically active substance generally being present in an amount from 5 to 95% w/w, the filler generally 5 to 90% w/w, the surface active agent generally 0.1 to 20% w/w and the auxiliary agent generally 0.01 to 10%. WG formulations may also be prepared without a filler or auxiliary agent.

UK Patent 1,304,543 describes four basic methods for preparing granular formulations. The four methods are extrusion; application of a surface coating onto a granule; absorbing an active substance into a granule; and finally applying a binder and active material to a suitable powder and forming granules from the powder mix.

The preparation of granules via an extrusion process is well known. Most of the known processes extrude a premix of active material and other ingredients under relatively high pressure, (and generally in excess of 100 psi), cut the spaghetti like extrudate into short lengths. These may be subsequently dried. An alternative process is disclosed in copending application PCT AU 88/00201 which uses low pressure extrusion (<30 psi) of a wet mix having relatively high levels of water. This leads to an extrudate of low compactness which readily breaks into small segments by gentle rolling or tumbling action which also tends to round the ends of the granules. Again these granules may be subsequently dried. Whilst these processes are generally satisfactory, when the active substance is a liquid the granules so formed tend to deteriorate on storage leading to poor dispersibility and suspensibility. Also dispersibility and suspersibility are adversely affected by storage, particularly at elevated temperatures.

Granules may also be prepared by coating a core granule with an absorbant coating of filler particles. A liquid active material may then be loaded onto the surface layer of the granules. Such a process is disclosed in NZ Patent 154,193 where the objective was to produce granules with reduced absorptive properties compared to granules prepared from minerals such as attapulgite. However these granules are designed for direct application to soil, pastures or other locus and as they have cores of particle size approximately 250 µm they would not be suitable for use as WG as the granule would not pass through the spray nozzle.

UK Patent 1,304,543 discloses a novel process wherein absorbant granules are prepared and subsequently liquid active substances are absorbed into the granules. However these compositions have granules which are calcined zeolites of several hundred microns in diameter. As with the NZ patent discussed above these granules will not disperse to produce the fine particles required for WG and are designed for direct application to the locus.

The fourth basic method of preparing granules involves a preliminary step of forming a wettable powder by blending the ingredients and milling them to provide the desired particle size. The wettable powder is then subsequently formed into granules by a range of techniques including agglomeration, spray drying, or other means such as pan granulation. Examples of such processes are also described by D A Hovde in the paper entitled "Laboratory Development and Evaluation of Water Dispersible Granules" presented at: ASTM E-35.22 Symposium on Pesticide Formulations and Application Systems: Third Symposium, Oct. 11–14, 1982, Fort Mitchell, Ky. While such processes are generally acceptable, it is not always possible to achieve good dispersibility and shelf life with all formulations especially with compositions where the biologically active agent is in a liquid state and relatively high levels of active agent are included in the granule.

There is thus a need for alternative granulation methods in order to enable a wider spectrum of liquid pesticides to be formulated in an effective and economical manner.

It is an object of this invention to provide a formulation method and formulations which will at least provide a useful alternative in the granulation art, but which in certain situations will provide a number of advantages over currently employed techniques.

SUMMARY OF INVENTION

The invention therefore provides in one aspect a water dispersible granule prepared by absorbing a liquid biologically active substance or adjuvant therefor, into an absorbent water dispersible granule prepared from filler particles in a finely divided state and a dispersing agent.

Another aspect the invention provides a method of preparing a water dispersible granule containing a biologically active substance or adjuvant therefor, comprising preforming a water dispersible granule comprised of finely divided filler particles and then loading a biologically active substance or adjuvant therefor in a liquid state and in a form that is miscible with water onto the preformed granule.

The invention further provides a water dispersible granule containing a biologically active substance or adjuvant therefor made by the above methods.

The invention further provides a method for changing a living organism comprising preforming an absorbent granule, adding the liquid biologically active substance as described above, dispersing the granule in water, and then applying the aqueous dispersion of the active substance in such a manner as to subject the living organism to the effect of that substance.

DETAILED DESCRIPTION OF THE INVENTION

In this specification, the term biologically active substance is used in its broadest sense to include not only the control of unwanted plants and animals but also substances which are applied to an animal or plant to achieve a beneficial effect. The substance can be, for example, a plant growth regulator or an animal growth regulator. In the case of plants, the pests will be weeds or other undesirable vegetation in a particular locus. In the case of animals, arthropods, nematodes and the like and larger animals such as rabbits, rats and mice and the like. Lower organisms are also included within the scope of the invention, particularly where they are harmful in a particular locus, such as fungi, algae and other micro-organisms. The term pesticides will include substances which control such pests, e.g. substances which destroy the pest but also substances which stop the pest from multiplying or reproducing. The term can thus cover herbicides, insecticides, molluscicides, nematicides, fungicides and the like.

The biologically active substance substance need not be an inanimate chemical entity, it can include micro-organisms which have a pesticidal effect, as that term has been used above, as well as organisms that have a beneficial effect.

The biologically active substance in accordance with this invention needs to be in a liquid state or formed into a liquid state, by for example dissolution in a suitable solvent or non-volatile compatible material, such as vegetable or mineral oils. The non-volatile compatible material may be another biologically active substance surface active agent or adjuvant therefor. Low melting point biologically active substances may be rendered suitable by using temperatures above their melting point for the process but this is not preferred. Whilst solvents or diluents may be used it is preferred however that the use of additional materials, particularly when they are volatile solvents is kept to a minimum to maintain the advantages over EC. If a solvent or diluent is used it is preferable that it does not cause the dispersant to be adversely effected.

The biologically active substance is preferably in a form in which it is miscible with the water. Where it is not inherently miscible with water, it will need to be made miscible preferably by addition of suitable emulsifiers or by use of a suitable solvent or cosolvent. In practice it is found that EC formulations of active substances with the omission of the carrier organic solvent are suitable for absorption into the absorbent granules. It is within the scope of the present invention for the active substance to be rendered water miscible after it has been added to the absorbent granules. This can be achieved by pre-adding or post-adding suitable surfactants to the granules. The surfactants are such that if pre-blended with the active ingredient, the mixture is water miscible.

In this invention, by the term miscible we mean that at the microscopic level the mixture of water and active ingredient is uniform and this may mean it can be in the form of a fine colloidal emulsion or suspension as well as a true solution.

The finely divided filler particles that are used to prepare the absorbent granules of this invention will normally be selected from inert mineral fillers but in some embodiments the fillers may also be biologically active.

The particle size of the finely divided filler will depend upon the ultimate use of the granule. When used in spray tanks with conventional spray equipment the filler will need to be of a size to ensure that it passes freely through the spray nozzles without blockage. The preferred particle size will be less than 150 μm. The most preferred range will be 1–50 μm. The filler materials should adhere also be of a type that do not of themselves adhere and form agglomerates that will not redisperse readily. Accordingly we have found precipitated silica is not preferred but can be tolerated at low levels. Agglomerability can be a function of the nature of the material as well as the methods of grinding or preparation of that material to a fine particle size. Preferred materials and the particles can be prepared using grinding or air separation techniques or combinations thereof.

Suitable substances for use as the finely divided filler include mineral earths and clays such as bentonite, kaolin, attapulgite, diatomaceous earth, zeolites, calcium carbonate, talc, muscovite mica and manufactured materials such as precipitated silicas and silicates, fused sodium potassium, aluminium silicate (heat processed perlite) or organic materials such as coals, lignites and plastics. The fillers are preferably water insoluble. The finely divided filler itself may be absorbent as in the case of diatomaceous earth, attapulgite or zeolites but this is not essential as it is the overall absorbency of the granule rather that of the individual particles that is important to the working of the invention. However, we have found that the overall absorbency of granules usually increases when absorbent particles are used.

Preferred materials include heat processed perlite, talc and muscovite mica, and combinations of such materials. It is believed the generally plate-like particle shape of these materials enables them to separate from each other more readily when granules, manufactured by extrusion, pan granulating or other means, are dispersed in water.

The absorbency of the granules is believed, without limiting the scope of the invention, to result in part from inclusions of voids between the finely divided particles. Accordingly the degree of packing will influence the degree of absorbency of the granules. The absorbency can also be varied by choosing different fillers that effect the packing. The degree of absorbency can be fine tuned further by using a mixture of different fillers. For example heat processed expanded perlite fillers tend to lead to highly absorbent granules while mica or talc fillers lead to less absorbent granules. The degree of absorbency of a granule can thus be varied by varying the ratio of heat processed perlite to mica.

The absorbancy of the granules may also be varied by adjusting the overall compactness of the granules. In the case of extrusion of wet premix the compactness is effected by both the pressure of extrudation and the amount of water present. Low pressure extrusion, for example 10–30 p.s.i. leads to highly absorbent granules.

It is important that the finely divided filler particles are water dispersible and this is achieved by including a dispersing agent. In a preferred form of the invention, the preformed granule will be formed from the finely divided filler and a dispersing agent selected such that it will dissolve on contact with a minimum amount of water. Generally this means the dispersant is at least 20% soluble in water.

The dispersing agent on the other hand will need to be an agent which is not adversely effected by physical or chemical reaction with the liquid biologically active substance. The biologically active substance can be a concentrated aqueous solution or suspension in which the amount of free water is insufficient to cause dissolution of the dispersant. The amount of dispersing agent will vary from a minimum, when it does not enable dispersion to occur in a reasonable period of time for application to a maximum where no greater benefit is achieved by increasing the amount. Generally, the amount of dispersing agent will range from 1–30% w/w of the absorbent granule and more preferably 5–15% w/w of granule.

Suitable dispersing or wetting agents include surface active agents and water soluble polymers, for example, lignosulphonate salts, polyacrylates and phosphate esters condensation products of formaldehyde, polyethylene glycol, and sugars. Suitable absorbent granules have been prepared with the following dispersing agent: "Morwet D425" (sodium naphthalene formaldehyde condensate ex Witco Corporation, USA) "Morwet EFW" Sulfated Alkyl Carboxylate and Alkyl Naphthalene Sulfonate—Sodium Salt "Tamol PP" (sodium salt of a phenolsulphonic acid condensate) "Reax 80N" (sodium lignosulphonate) "Wettol D1" sodium alkylnaphthalene sulphonate (ex BASF). Generally the dispersing or wetting agents are anionic surfactants.

The use of special binding agents is not generally necessary as the binding ability of the dispersing agent is generally adequate but binding agents may prove useful in certain formulations and are embraced within the scope of the present invention. Suitable binding agents may be selected from a range of natural or synthetic gums, sugars, and polymers. Materials that do not swell rapidly upon hydration or become viscous are preferred.

Additional auxiliary agents such as surfactants and disintegrating agents may be added where desired to modify the properties of the granules.

The materials comprising the preformed granule may be combined in any sequence and blended in a suitable blender and granulated using known methods and equipment for making granules. For example, the finely divided filler and dispersant may be blended together with water being added either before, during or after the blending of the dry ingredients. Alternatively the dispersant may be dissolved first in the water used for blending. After formation of the granules, they are then dried to remove the excess moisture.

The amount of water used will vary depending on the desired absorptive capacity of the inert granules which is also controlled by varying the ratio of the fillers.

Granulating conditions and the type and level of dispersant used will also have an influence on the amount of water required.

Typically the amount of water may range from 5 kg–150 kg per 100 kg dry mix (fillers and dispersant) and more typically is 20–70 kg water/100 kg dry mix.

Granules can be dried by any suitable means (e.g. on trays) that does not result in attrition or damage. Band or static bed dryers are satisfactory. A fluid bed dryer is preferred because of its relative efficiency.

To ensure satisfactory physical stability (and to avoid degradation of the loaded product) granules are preferably dried to a moisture content of not more than 1.0% w/w (as loss on drying). Temperature during drying is preferably controlled to a low temperature such as below 50° C.

Performed granules can be stored and then used to take up a predetermined amount of the liquid biologically active substance at an appropriate time and place. The invention thus enables a granulating plant to be established at a most appropriate place to service a particular area while loading plants where the granules are loaded with the active substances can be sited closer to the end user. Loading of the substance can take place in any suitable apparatus. The apparatus will deliver the liquid substance to the agitated granules in such a manner that the liquid is taken up uniformly amongst all granules without damaging the granules. A suitable apparatus can therefore be a rotating cylinder, for example a Diosna universal mixer ex Dierks and Sohne GmbH & Co KG, a cone mixer with the liquid substance being delivered rapidly to the preformed granules via spray nozzles in a manner to distribute the substance over the surface of the absorbent granules as quickly as possible. The spray can be introduced through air atomising nozzles to ensure even spread of the liquid active substance the granules. Flat spray jets will in some cases be appropriate. Other means of delivering the liquid in the manner required can also be used. The amount of liquid substance that is absorbed onto the granule will vary dependent upon the desired end use.

It is preferred in loading the preformed granules with the liquid that a uniform loading per granule is achieved. Equilibration between unevenly loaded granules is believed to take place but this may take substantial periods of time. Where the absorbency of the granule is to be substantially fully saturated then the liquid can simply be poured onto the granules and granules agitated until they become fully saturated. It has been found that in some cases a fully saturated granule may not disperse in water as rapidly as do partially saturated granules.

It is therefore preferred to partially saturate the granules. For example, when the loading capacity is 40% it is preferred to only lead to 32%, i.e. 80% of its capacity. It is preferably to load the granules to 60–90% and more preferably 70–85% of their capacity. Besides using the spraying techniques such as air atomising nozzles, it is possible to cool the liquid to increase its viscosity so that it does not flow into the granules so quickly. Agitation of the granules in the cooled liquid will lead to an even spread of the liquid over each granule and as the temperature rises absorption by each granule of its liquid coating and hence granules of uniform absorption.

The invention has as one of its advantages the ability to provide granules with a high carrying capacity for the biologically active substance. The maximum amount of liquid substance that can be incorporated will be limited by the absorptive capacity of the granules. Levels of up to 40% w/w active substance to dry granule are achievable with the process of the present invention.

Preferably the biologically active substance will be mixed with an emulsifier to form an emulsifiable concentrate in a liquid form which can then be absorbed onto the preformed granule. Alternatively, the liquid substance can be dissolved in a suitable solvent, selected such that the solution is miscible with water, and then be absorbed onto the granule. The amount of solvent used in such a situation will be as low as possible in order to enable loading as high a concentration of the active substance into each granule as may be desired. If the liquid substance is miscible with water in its natural state, then it can be loaded onto the preformed granules without further modification.

Where the liquid active is not miscible with water, but is able to be rendered so by the addition of a suitable emulsifier it is possible for the surfactant and active material to be absorbed sequentially into the granules rather than as a premix. It is also possible for the granules to be prepared with the emulsifier present and the liquid active substance is then subsequently absorbed into the granules. Dispersibility is still maintained in these variations.

Suitable biologically active substances for the water dispersible granules of the present invention are liquid at ambient temperature of from 5°–50° C. but this is not essential. A number of actives, e.g. Lambda-cyhalothrin (mp 49) is a solid at ambient temperature, but can be converted to a liquid form (usually by warming) in admixture with suitable liquid emulsifiers, solvent or other non aqueous liquids. We have found the actives most suitable for the working of this invention have low water solubility, less than 20 g/liter. It is believed in some cases this may aid the dispersibility of the filler particles as the dispersant is usually insoluble in such actives.

Examples of suitable pesticides are set out in the following table where all the pesticides are liquids at 25° C. apart from Lamda-cyhalothrin which is a solid at 25° C.

| Chemical | Type | Solubility in water |
|---|---|---|
| Acetochlor | Herbicide | 223 mg/l |
| Butachlor | Herbicide | 23 mg/l |
| Butylate | Herbicide | 46 mg/l |
| Chlorfenvinphos | Insecticide | 145 mg/l |
| Chlorimephos | Insecticide | 60 mg/l |
| Diazinon | Insecticide | 40 mg/l |
| Dinocap | Acaricide Fung. | (Sp. soluble) |
| Fenitrophion | Insecticide | 14 mg/l |
| Fluazifop-P-butyl | Herbicide | 1 mg/l |
| Fonofos | Insecticide | 13 mg/l |
| Heptopargil | Plant growth Regulator | 1 g/l |
| Isofenphos | Insecticide | 23.8 mg/l |
| Lambda-cyhalothrin | Insecticide | 0.005 mg/l |
| Mecarbam | Acaricide Insect. | <1 gm/l |
| Metolachlor | Germination Inhib. | 530 mg/l |
| Omethoate | Acaricide Insect. | 0.5 g/l |
| Pebulate | Herbicide | 60 mg/l |
| Pirimiphos-methyl | Acaricide Insect | 5 mg/l |
| Propetamphos | Insecticide | 110 mg/l |
| Propargite | Acaracide | 1.9 mg/l |
| Prosulfocarb | Herbicide | 13.2 mg/l |
| Pyraclofos | Insecticide | 33 mg/l |
| Sulprofos | Insecticide | <5 mg/l |
| Thiobencarb | Herbicide | 30 mg/l |
| Triazophos | Acaricide Insect. | 30–40 mg/l |
| Bromophos-ethyl | Insecticide | 0.14 mg/l |
| Butamifos | Herbicide | 5.1 mg/l |
| Carbophenothion | Acaricide Insect. | <1 mg/l |
| Cyhalothrin | Insecticide | 0.003 mg/l |
| Demeton-S-methyl | Insecticide | 3.3 g/l |
| Dichloruos | Insecticide | 10 g/l |
| Disulfoton | Acaricide Insect. | 25 mg/l |
| Fenpropimorph | Fungicide | 10 mg/l |
| Heptenophos | Insecticide | 2.2 g/l |
| Hydroprene | Insect growth reg. | 0.54 mg/l |
| Malathion | Acaracide Insect. | 145 mg/l |
| Mephosfolan | Insecticide | 57 mg/l |
| Molinate | Herbicide | 880 mg/l |
| Parathion | Acaricide Insec. | 24 mg/l |
| Permethrin | Insecticide | 0.2 mg/l |
| Profenofos | Insecticide | 20 mg/l |
| Propiconazole | Fungicide | 110 mg/l |
| Prothiofos | Insecticide | 1.7 mg/l |
| Pyrifenox | Fungicide | 115 mg/l |
| Tebutam | Herbicide | Almost Insoluble in water |
| Thiometon | Insecticide | 200 mg/l |
| Tridemorph | Fungicide | 11.7 mg/l |

The preferred liquid biologically active substances are propargite, fluazifop-P-butyl and Lambda-cyhalothrin.

The emulsifiers that can be used in accordance with the invention will depend on the liquid pesticide and will usually be chosen such that they would form an acceptable EC when combined with the active ingredient. In most cases binary or even tertiary mixtures of suitable emulsifiers are used.

Emulsifiers chosen should be compatible with the liquid active and other components of the formulation. A preferred characteristic is that they do not (at the level incorporated) cause the liquid active to solidify. Some liquid actives are completely miscible in water and may not require an emulsifier. Emulsifier may be used at rates ranging from say 1–75% w/w of the EC active ingredient.

Preferred emulsifiers for propargite and fluazipfop-P-butyl are:

"Teric 200" (alkyl phenol propylene oxide/ethylene oxide condensate)

"Kemmat SC 15B" (calcium salt of dodecyl benzene sulphonate).

These emulsifiers are usually used in admixture. The actual ratio varies depending on the liquid active. Emulsifiers can be of the anionic, cationic or non-ionic type.

Examples of the anionic type include soaps, salts of aliphatic monoesters or sulphuric acid such as sodium lauryl sulphate, salts of sulphonated aromatic compounds, for example sodium dodecylbenzenesulphonate, sodium, calcium or ammonium lignosulphonate, alkyl naphthalene sulphonates such as salts of diisopropyl- and 10 triisopropylnaphthalene sulphonates, phosphate esters, sulphosuccinates and mixtures thereof. Suitable agents of the non-ionic type include, for example, the condensation products of ethylene oxide with fatty alcohols such as oleyl alcohol or cetyl alcohol, e.g. tridecyl alcohol ethoxylate, or with alkyl phenols such as octyl phenol, nonyl phenol and octyl cresol. Other non-ionic agents are the partial esters with ethylene oxide and the lecithins and phosphorylated surfactants such as phosphorylated ethylene oxide/propylene oxide block copolymer and ethyoxylated and phosphorylated styryl substituted phenol.

In accordance with a further feature of the invention, the preformed absorbent granules can be used to absorb liquid adjuvants which in accordance with this invention are substances designed to enhance the effect of the biologically active substance. Thus adjuvants can include substances which assist in penetration of the active agent into a plant in the case of a systemically active pesticide. The adjuvant can be incorporated with the liquid biologically active substance where the adjuvant and the substance are mutually compatible and remain so or alternatively a preformed granule can be loaded with a biologically active substance and then be subsequently loaded with an adjuvant. Alternatively, the biologically active substance can be loaded into a first sample of the preformed granules and the adjuvant loaded into a second sample and these two samples added to water for spraying.

It is also within the scope of the invention for a solid biologically active substance to be used as the finely divided filler, as long as the biologically active substance is miscible or can be rendered miscible in water. The preformed granule containing the biologically active substance can then be used to absorb an adjuvant which is an enhancer for that particular biologically active substance. The substance in this aspect of the invention need not be the sole finely divided filler used to make the granules, mixtures with other biologically active substances which are mutually compatible or with other finely divided powders may also be employed. The preformed granule containing the biologically active substance can also be used to absorb another biologically active substance in liquid form.

The method by which the granules are formed in accordance with the invention is not particularly critical. However the type of granulation technique used may effect the absorbancy of the granules. For example, we have found the granulation technique described in our copending application PCT/AU 88/00201 to be particularly advantageous.

The following Examples illustrate various features of the invention:

EXAMPLE 1

Preparation of 30% w/w active content Fluazifop-P-butyl herbicide.

(a) Absorbent Granule Formula

| Ingredient | % w/w |
| --- | --- |
| Perlite SP412 (Diaclite 412 ex Induplex Inc. Philippines) | 45 |
| Mica 20 (20 micron) (Mintech (NZ) Ltd) | 45 |
| Reax 80N (Westvaco Pacific Pty Ltd North Sydney Sodium Lignin sulphonate) | 10 |

(b) Active Substance Formula

| Ingredient | % w/w |
| --- | --- |
| Fluazifop-P-butyl Tech. grade (90.9% a.i.) | 88.0 |
| Teric 200 (ICI Australia, poly propylene ethylene oxide surfactant | 9.6 |
| Kemmat SC15 (Calcium dodecyl benzene sulphonate emulsifier) Harcros Industrial Chemicals, NSW | 2.4 |

(c) Finished Product Composition

| Component | % w/w |
| --- | --- |
| Absorbent granules | 56.24 |
| Active substance formulation | 43.76 |

(d) Finished Product Formula

| Ingredient | % w/w |
| --- | --- |
| Fluazifop-P-butyl, tech grade | 38.509 |
| Perlite SP412 | 25.308 |
| Mica 20 | 25.308 |
| Reax 80N | 5.625 |
| Teric 200 | 4.200 |
| Kemmat SC15B | 1.050 |

The absorbent granules were prepared by adding water to the granule pre-mix at a ratio of 47 liters per 100 kg of dry mix and using the process of Example 1 of PCT/AU/88/00201. In that example a wet premix is extruded from a reciprocating low pressure (20 psi) extruder to give a low compact extruder which is broken and rounded into granules by a gentle rolling action. The granules were dried and the active substance formulation was added to the granules to give a loading of 80% of the available absorptivity. The total loading capacity of a granule is determined by monitoring the addition of a mobile oil to a sample of granules and assessing the free flowability of the samples. Maximum absorption is deemed to be the point at which free flowability ceases. The test is preferably completed over a 10 minutes test period to enable consistent results to be achieved.

EXAMPLE 2

Preparation of 25% w/w active content Fluazifop-P-butyl herbicide.

(a) Absorbent Granule Formula

| Ingredient | % w/w |
| --- | --- |
| Mica 20 | 60 |
| Perlite SP412 | 30 |
| Reax 80N | 10 |

(b) Active Substance Formula

| Ingredient | % w/w |
| --- | --- |
| Fluazifop-P-butyl Tech. grade (90.9% a.i.) | 88 |
| Teric 200 | 9.6 |
| Kemmat SC15 | 2.4 |

(c) Finished Product Composition

| Component | % w/w |
| --- | --- |
| Absorbent granule | 68.74 |
| Active substance formulation | 31.26 |

(d) Finished Product Formula

| Ingredient | % w/w |
| --- | --- |
| Fluazifop-P-butyl, tech grade | 27.510 |
| Mica 20 | 41.244 |
| Perlite SP412 | 20.622 |
| Reax 80N | 6.874 |
| Kemmat SC15B | 0.750 |
| Teric 200 | 3.000 |

The process of Example 1 was repeated to provide granules with 25% w/w Fluazifop-P-butyl herbicide.

EXAMPLE 3

Preparation of 30% w/w active content Propargite aracide (a) Absorbent Granule Formula

| Ingredient | % w/w |
| --- | --- |
| Mica 20 | 50 |
| Perlite SP412 | 40 |
| Reax 80N | 10 |

(b) Active Substance Formula

| Ingredient | % w/w |
| --- | --- |
| Propargite, technical grade (85.1% a.i) | 90.0 |
| Teric 200 | 7.0 |
| Kemmat SC15 | 3.0 |

-continued (c) Finished Product Composition

| Component | % w/w |
|---|---|
| Absorbent granules | 60.83 |
| Active substance formulation | 39.17 |

(d) Finished Product Formula

| Ingredient | % w/w |
|---|---|
| Propargite, tech. grade | 35.253 |
| Mica 20 | 30.415 |
| Perlite SP412 | 24.332 |
| Reax 80N | 6.083 |
| Teric 200 | 2.742 |
| Kemmat SC15 | 1.175 |

The process of Example 1 was used to provide granules with 30% Propargite aracide.

EXAMPLE 4

Preparation of 30% active content Fluazifop-P-butyl herbicide.

(a) Absorbent Granule Formula

| Ingredient | % w/w |
|---|---|
| Perlite SP412 | 50 |
| Mica 20 | 40 |
| Tamol PP (ex BASF) (Sodium salt of phenolsulphonic acid condensation product). | 10 |

(b) Active Substance Formula

| Ingredient | % w/w |
|---|---|
| Fluazifop-P-butyl Tech. grade (90.9% a.i.) | 88 |
| Teric 200 | 9.6 |
| Kemmat SC15 | 2.4 |

(c) Finished Product Composition

| Component | % w/w |
|---|---|
| Absorbent granules | 62.49 |
| Active substance formulation | 37.51 |

The process of Example 1 was used to provide granules with 30% Fluzifop-P-butyl herbicide.

EXAMPLE 5

Preparation of 30% active content Fluazifop-P-butyl herbicide with different surfactant in the absorbent granule.

(a) Absorbent Granule Formula

| Ingredient | % w/w |
|---|---|
| Perlite SP412 | 50 |
| Mica 20 | 38 |
| Lomar PWM (Sodium salt of condensed Naphthalene sulfonic acid (Henkel Corporation, USA). | 12 |

(b) Active Substance Formula

| Ingredient | % w/w |
|---|---|
| Fluazifop-P-butyl Tech. grade (90.9% a.i.) | 88 |
| Teric 200 | 9.6 |
| Kemmat SC15 | 2.4 |

(c) Finished Product Composition

| Component | % w/w |
|---|---|
| Absorbent granules | 62.49 |
| Active substance formulation | 37.51 |

The process of Example 1 was repeated to provide granules with 30% Fluzifop-P-butyl herbicide.

EXAMPLE 6

Preparation of 30% active content Fluzifop-P-butyl herbicide using fillers that differ from Example 5.

(a) Absorbent Granule Formula

| Ingredient | % w/w |
|---|---|
| Perlite SP412 | 50 |
| Talc Superfine 15 | 40 |
| Morwet D425 | 10 |

(b) Active Substance Formula

| Ingredient | % w/w |
|---|---|
| Fluazifop-P-butyl Tech. grade (90.9% a.i.) | 88 |
| Teric 200 | 9.6 |
| Kemmat SC15B | 2.4 |

(c) Finished Product Composition

| Component | % w/w |
|---|---|
| Absorbent granules | 62.49 |
| Active substance formulation | 37.51 |

The process of Example 1 was repeated to provide granules with 30% Fluzifop-P-butyl herbicide.

EXAMPLE 7

Preparation of 30% active content Fluzifop-P-butyl herbicide using the process of Example 1 but varying the filler composition of the absorbent granule.

(a) Absorbent Granule Formula

| Ingredient | % w/w |
|---|---|
| Talc Superfine 15 | 75 |
| Microcel E | 15 |
| Morwet D425 | 10 |

(b) Active Substance Formula

| Ingredient | % w/w |
|---|---|
| Fluazifop-P-butyl Tech. grade (90.9%. a.i.) | 88 |

|   |   |
|---|---|
| Teric 200 | 9.6 |
| Kemmat SC15B | 2.4 |

(c) Finished Product Composition

| Component | % w/w |
|---|---|
| Absorbent granules | 62.49 |
| Active substance formulation | 37.51 |

EXAMPLE 8

Manufacture of water dispersible granules comprising 25% to 30% a.i. w/w Fluzifop-P-Butyl from inert absorbent granules prepared by different methods.

A 15 kg batch of absorbent granule premix was prepared as follows:

(Finished product formula, dry weight basis)

| Ingredient | % w/w |
|---|---|
| Perlite SP412 | 55 |
| Talc 'Superfine 15' (ex Commercial Minerals Ltd, Aust) (95% <15M). | 35 |
| 'Ultrazine NA' (Sodium lignosulphonate ex Borregaard, Norway) | 10 |

Water was added to the premix at the rate of 600 g/kg dry material.

Method

The perlite and talc were added to a ribbon blender and blended dry for 5 minutes.

The 'Ultrazine NA' was first dissolved in 75% of the water and delivered from a pressure vessel to the dry mix in the ribbon blender via spray nozzles. The balance of the water was applied by the same means. This served to flush the liquid delivery system and ensure all the 'Ultrazine NA' was conveyed to the premix.

The damp premix was blended for a total of 10 minutes in 2 minute cycles. At the end of each cycle the blender was stopped to clear material from the ribbons and other surfaces where build up had occurred. This was to ensure that the final damp mixture was reasonably homogenous.

Granulation Trial No. 1

5 Kg of the damp premix was passed through a small hammermill fitted with a 12.5 mm aperture screen to reduce the few agglomerates of over-damp material present.

The damp hammermilled premix was placed in a 600 mm dia. granulating bowl rotating at 27 rpm.

Water was applied to the tumbling mass of damp powder as a fine spray from a hand operated spray gun fitted with an air atomizing nozzle. A large spatula was used occasionally to remove loose build up from the walls of the bowl.

The premix agglomerated readily and the water overspray was discontinued when granules of approximately the desired size had formed. These were dried on a static bed dryer at a temperature not exceeding 50 deg. C.

A dry sieve analysis was carried out on a representative sample of the dried granules by subjecting them to 10 minutes on a 'Rotap' sieve shaker.

Results

| Sieve (aperture size) | % w/w retained (cumulative) |
|---|---|
| +2057 μm | 13.6 |
| −2057 + 1180 μm | 15.4 |
| −1180 + 710 μm | 52.4 |
| −710 + 425 μm | 14.8 |
| −425 + 150 μm | 3.6 |
| −150 μm | 0.2 |

Granules sized −110+710 μm were removed from the main sample by screening and retained for loading with emulsifiable fluazifop-P-butyl.

Moisture tests were carried out on damp and dried material, results as follows:

|   | Moisture Content (as loss on drying) |
|---|---|
| Damp premix after hammermilling | 37.7% |
| Wet granules | 42.7% |
| Dried granules | 1.24% |

Granule Loading

A sample of water dispersible granules comprising 25% a.i. w/w emulsifiable fluazifop-P-butyl was prepared in the laboratory as follows:

Fluazifop-P-butyl formula:

| Ingredient | % w/w |
|---|---|
| Fluazifop-P-butyl technical grade @ 88.3% a.i. w/w | 88.0 |
| 'Teric 200' | 9.6 |
| Kemmat HF60 | 2.4 |
| Loading Recipe |  |
| Absorbent granules | 67.8 |
| Fluazifop-P-butyl formulation | 32.2 |

A 500 g sample of above was prepared by adding the granules to pre-weighed emulsifiable fluazifop-P-butyl in a polythene bag, sealing the end of the bag by twisting and mixing the contents vigorously by hand. The granules appeared 'wet' initially but became free flowing after approximately 60 seconds as the liquid was absorbed.

Laboratory tests were carried out on the loaded granules initially and after periods of storage at a constant 50 deg. C.

| Initial Test Results |   |
|---|---|
| Time to disperse | 165 seconds |
| Suspensibility (total solids) | 85% |
| Wet sieve analysis of dispersed granules (% retained, cumulative) |  |
| 150 μm | 0.009 |
| 53 μm | 0.014 |

Granulation Trial No. 2

The balance of the damp premix prepared for granulation trial No. 1 was taken direct from the blender and passed through a vertical paddle mixer where it was converted to a soft 'dough'. This dough passed from the base of the paddle mixer via a 6 mm aperture mesh to form large soft extrusions. The extrusions were dried on a static bed at a temperature not exceeding 50 deg. C. before being passed through a 'Manesty Rotor-gran' fitted with a 1.31 mm aperture mesh.

The action of the 'Manesty Rotor-gran' reduced the dried extrusions to angular granules (chips) of different sizes from which product within the −1180+710 μm size range was removed by screening. This was subsequently loaded with emulsifiable fluazifop-P-butyl in the manner described for trial No. 1.

Laboratory tests were carried out on the loaded granules initially and after periods of storage at 50 deg. C.

| Initial Test Results | |
|---|---|
| Time to disperse | 150 seconds |
| Suspensibility (total solids) | 88% |
| Wet sieve analysis of dispersed granules (% retained, cumulative) | |
| 150 μm | 0.003 |
| 53 μm | 0.004 |

EXAMPLE 9

This Example illustrates the preparation of water dispersible granules of two samples. 9A and 9B comprising 30% w/w Diazinon. It was prepared in the laboratory as follows:

| | % w/w |
|---|---|
| Diazinon Formulation Ingredient | |
| Diazinon Technical Grade @ 95% AI | 90 |
| Teric 200 | 5 |
| Kemmat HF 60 | 5 |
| Granule Composition 9A | |
| Perlite SP 412 | 55 |
| Talc Superfine 15 | 35 |
| Supragil MNS 90 | 10 |
| Granule Composition 9B | |
| Perlite SP 412 | 55 |
| Talc Superfine 15 | 35 |
| Ultrazine NA | 10 |
| Loading Recipe for 9A & 9B Ingredient | |
| Absorbent Granules | 64.91 |
| Diazinon formulation | 35.09 |

A 500 gram sample of the above was prepared by adding 324.55 gram of granules to 175.45 grams of diazinon formulation in a polythene bag. The end of the bag was sealed by twisting and the contents were thoroughly mixed by hand.

The granules appeared wet initially but became free-flowing after approximately 30 seconds as the liquid was absorbed.

| Final Formulation Details | |
|---|---|
| Ingredient | % w/w |
| Diazinon 300 9A | |
| Perlite SP 412 | 35.71 |
| Talc Superfine 15 | 22.72 |
| Supragil MNS 90 | 6.49 |

| -continued | |
|---|---|
| Diazinon Technical Grade @ 95% AI | 31.58 |
| Teric 200 | 1.75 |
| Kemmat HF 60 | 1.75 |
| Diazinon 300 9B | |
| Perlite SP 412 | 35.71 |
| Talc Superfine 15 | 22.72 |
| Ultrazine NA | 6.49 |
| Diazinon Technical Grade @ 95% | 31.58 |
| Teric 200 | 1.75 |
| Kemmat HF60 | 1.75 |

| | Laboratory Test Results Initial | |
|---|---|---|
| Sieve Tests | % Retained 150 mm | % Retained 53 mm |
| Diazinon 300 9A | 0.008 | 0.012 |
| Diazinon 700 9B | 0.012 | 0.033 |
| Dispersion | | |
| Diazinon 300 9A | 80 seconds | |
| Diazinon 300 9A | 105 seconds | |
| Suspensibility | | |
| Diazinon 300 9A | 75.3% | |
| Diazinon 300 9B | 90.1% | |

EXAMPLE 10

Preparation and biological testing of 25% active content Fluazifop-P-butyl herbicide.

| Ingredient | % w/w |
|---|---|
| Active Substance Formula | |
| Fluazifop-P-butyl (Tech. grade) | 88 |
| Teric 200 | 9.6 |
| Kemmat HF 60 | 2.4 |
| Absorbent Granule Recipe | |
| Perlite SP 412 | 55 |
| Talc superfine 15 | 35 |
| Ultrazine NA | 10 |

Loading Ratio

Fluazifop-P-butyl Tech. Grade AI 88.3%. Active substance formulation AI 77.704%.

Active substance formulation @ 77.704% AI=32.2 g/100

Absorbent granule=67.8 g/100

| Final Formulation | |
|---|---|
| Ingredient | % w/w |
| Fluazifop-P-butyl (Tech Grade) | 28.34 |
| Perlite SP 412 | 37.29 |
| Talc superfine 15 | 23.73 |
| Ultrazine NA | 6.78 |
| Teric 200 | 3.09 |
| Kemmat HF 60 | 0.77 |

Granules were prepared as in Example 1 using 32 liters of water per 100 kg of dry premix.

Biological Evaluation

Chemical treatments were applied post emergence to barnyard grass (*Echinochioa crus-galli*) at the three leaf to three tiller stage and to soybeans at the 1 to 2 trifoliate leaf stage.

The barnyard grass density was 176 plants/m² of which 21% were tillered.

RESULTS

Visual estimates of percent control of barnyard grass were made 27 DAA (days after application) and panicle counts were made 56 DAA.

Visual estimates of percent crop damage were made 27 and 56 DAA and of percent crop cover 27 DAA.

Barnyard Grass (Table 1)

At 27 DAA, the WG treatments were slightly more active than the EC. However, there was no difference between any of the treatments at 56 DAA when they all gave excellent reduction (>97%) in seed head counts.

At all of these assessments there were no significant differences between spray treatments.

TABLE 1

Fluazifop-P-butyl herbicides WG, comparison of formulations on barnyard grass in soybeans at 187.5 GAI/HA
Location: Coree South, Southern N. S. W

| Treatment | % Control | Seed Heads/M2 |
| --- | --- | --- |
| | 27 DAA Means | 56 DAA Means *1 |
| Untreatment control | 0 | 161.4 |
| Application Date: 03/02/91 | | |
| Spray volume: 100 L/HA | | |

EXAMPLE 11

This example shows the preparation of 12.5% w/w active content Fluazifop-P-butyl herbicide with a mineral oil also present in the granule (a) Absorbent Granule Formula

| Ingredient | % w/w |
| --- | --- |
| Perlite SP 412 | 55 |
| Mica 20 | 25 |
| Morwet EFW (Napthalene Sulphonate) | 10 |
| Ultrazine NA | 10 |

(b) Active Substance Formula

| Ingredient | % w/w |
| --- | --- |
| Fluazifop-P-butyl Tech. grade (88.3% a.i.) | 43.4 |
| Teric 200 | 12.5 |
| Tween 20 (polyethylene sorbitan fatty acid ester) | 19.8 |
| Prosol P12 (mineral oil, ex Caltex) | 24.3 |

(c) Finished Product Composition

| Component | % w/w |
| --- | --- |
| Absorbent granules | 67.3 |
| Active substance formulation | 32.7 |

The granules (12.5% w/w active) were prepared as for Example 5.

EXAMPLE 12

This example shows the preparation of a 25% w/w active content Fluzifop-P-butyl herbicide where the active substance formula has alternative surfactants to that used in Example 11. The granules were prepared as for Example 11, using the same weight amounts and process except that the active substance formula was as follows:

| Ingredient | % w/w |
| --- | --- |
| Fluazifop-P-butyl (Tech. grade) | 88 |
| Soprophor 4D/384 (Sulfahed polyarylphenol ethoxyate ex Rhone-Poulenc) | 12 |

EXAMPLE 13

This example illustrates the use of an active substance that is normally solid but is applicable to the present invention by transforming the active substance to liquid form. This example shows the preparation of a 5% w/w Lambda-cyhalothrin active substance.

(a) Absorbent Granule Formula

| Ingredient | % w/w |
| --- | --- |
| Perlite SP 412 | 55 |
| Mica 20 | 25 |
| 1) Wettol DI | 15 |
| 2) Wettol NTI | 5 |

(b) Active Substance Formula

| Ingredient | % w/w |
| --- | --- |
| Cotton seed oil | 53 |
| Lambda cyhalothrin, technical grade @ 89.9% a.i. | 35 |
| 3) Teric 17A2 | 10.8 |
| 4) Teric 17A3 | 1.2 |

Loading Formula

| | |
| --- | --- |
| Absorbent granule | 84.1% |
| Active substance formulation | 15.9% |

1) Sodium salt of a phenol-sulphonic acid condensation product - dispersing agent supplied by BASF.
2) Sodium alkylnapthalene sulphonate - wetting agent supplied by BASF.
3) Cetyl-oleyl alcohol ethoxylate - emulsifier supplied by ICI Australia.
4) Cetyl-oleyl alcohol ethoxylate - emulsifier supplied by ICI Australia.

The Active ingredient formulation is prepared by warming all the ingredients to 50 deg. C. Upon cooling to ambient temperature the formulation remained in a liquid state.

The absorbent granule manufacturing process and loading procedure were as set out in Example 1.

While in accordance with the invention specific features may have been mentioned, the invention is not to be construed as being limited thereto. Furthermore where materials and steps have been described, and known equivalents exist thereto, such known equivalents are incorporated herein as if specifically set forth.

We claim:

1. A method for preparing water dispersible granules by preparing an absorbent water dispersible granule from finely divided filler particles and an organic dispersing agent and then absorbing a liquid biologically active substance or adjuvent therefor into said absorbent granule.

2. A method for preparing water dispersible granules as defined in claim 1 wherein the biologically active substance or adjuvent therefor is in a form that is miscible with water.

3. A method for preparing water dispersible granules as defined in claim 2 wherein the biologically active substance is a liquid at less than 50° C.

4. A method for preparing water dispersible granules as defined in claim 3 wherein the biologically active substance has a water solubility of less than 20 g/liter.

5. A method for preparing water dispersible granules as defined in claim 4 wherein the finely divided fillers are water insoluble and have particle size less than 50 micron.

6. A method for preparing water dispersible granules as defined in claim 5 wherein at least a portion of the fillers are plate-like in shape.

7. A method for preparing water dispersible granules as defined in claim 1 wherein a portion of the filler is selected from heat processed expanded perlite, talc and muscovite mica.

8. A process for preparing water dispersible granules as defined in claim 1 wherein the granules are formed by a low pressure extrusion process followed by gentle rolling or tumbling action.

9. A process for preparing water dispersible granules as defined in claim 1 wherein the quantity of biologically active substance or adjuvant therefore that is absorbed into the absorbent granule is chosen such that 60–90% of the absorptive capacity of the absorbent granules is attained.

10. A process for preparing water dispersible granules as defined in claim 1 wherein the active substance is selected from the group consisting of fluazifop-P-butyl, Lambda-cyhalothrin and propargite.

11. A method according to claim 1 wherein the dispersing agent is a surfactant.

12. A method according to claim 1 wherein the dispersing agent is a surface active agent or a water-soluble polymer.

13. A method according to claim 12 wherein the polymer is selected from the group consisting of lignosulphonate salts, polyacrylates, and phosphate esters, condensation products of formaldehyde, polyethylene glycol, and sugars.

14. A method for preparing water dispersible granules which carry a biologically active substance, said method comprising preparing absorbent water-dispersible granules from a blend of finely divided, water-insoluble filler particles and an organic polymeric dispersing agent which is at least 20% soluble in water, said finely divided filler being selected from the group consisting of mineral earths, clays, silicas and silicates and thereafter absorbing a liquid biologically active substance into said absorbent granules, said biologically active substance having a water-solubility of less than 20 g/liter, the amount of biologically active substance which is absorbed not exceeding the amount that maintains the granule in a free-flowing condition.

15. The method of claim 14 wherein the filler comprises heat processed perlite, talc and muscovite mica.

16. The method of claim 14 wherein the dispersing agent comprises lignosulphonate salts, polyacrylates, phosphate esters, condensation products of formaldehyde, polyethylene glycol, and sugars.

* * * * *